US00PP26677P3

(12) United States Plant Patent
Austin

(10) Patent No.: US PP26,677 P3
(45) Date of Patent: May 3, 2016

(54) SHRUB ROSE PLANT NAMED 'AUSYACHT'

(50) Latin Name: *Rosa hybrida*
Varietal Denomination: AUSyacht

(71) Applicant: David Austin Roses Ltd., Albrighton, Wolverhampton (GB)

(72) Inventor: David J. C. Austin, Wolverhampton (GB)

(73) Assignee: DAVID AUSTIN ROSES LTD., Albrighton, Wolverhampton (GB)

( * ) Notice: Subject to any disclaimer, the term of this patent is extended or adjusted under 35 U.S.C. 154(b) by 148 days.

(21) Appl. No.: 13/999,976

(22) Filed: Apr. 11, 2014

(65) Prior Publication Data

US 2015/0074861 P1 Mar. 12, 2015

(30) Foreign Application Priority Data

Sep. 11, 2013 (QZ) ..... 2013/2369

(51) Int. Cl.
*A01H 5/02* (2006.01)

(52) U.S. Cl.
USPC ..... Plt./108
CPC ..... *A01H 5/0222* (2013.01)

(58) Field of Classification Search
USPC ..... Plt./108
See application file for complete search history.

*Primary Examiner* — Keith Robinson
(74) *Attorney, Agent, or Firm* — KPPB LLP

(57) ABSTRACT

A variety of rose plant of the shrub class, named 'AUSyacht'. The 'AUSyacht' is a variety of a rose suitable for cut-flower production with double, deep red blooms having many petals in the character of an old-fashioned garden shrub rose.

1 Drawing Sheet

Classification: The present invention relates to a new *Rosa hybrida* shrub of the market class 'English Rose'.

Variety denomination: The new plant has the varietal denomination 'AUSyacht'.

ORIGIN OF INVENTION

This invention relates to a new and distinct variety of shrub rose plant named 'AUSyacht', which was originated from the cross-pollination of the two unnamed and unpatented seedlings of *Rosa hybrida.*

BACKGROUND OF THE INVENTION

The primary objective of this breeding was to produce a rose variety suitable for cut-flower production with double, deep red blooms having many petals in the character of an old-fashioned garden shrub rose.

SUMMARY OF THE INVENTION

Among the features which distinguish the new variety from others presently available and commercial rose cultivars known to the inventor is the following combination of characteristics: deep red, medium-large, saucer-shaped blooms having many petals.

Asexual reproduction of the new variety by budding as performed at Bowling Green Lane in Albrighton, Britain shows that the foregoing and other distinguishing characteristics come true to form and are established and transmitted through succeeding asexual propagations. 'AUSyacht' may be asexually propagated by budding. The budding successfully occurred on the plant/rootstock *Rosa* 'Inermis' for the observed plants.

COMPARISON WITH PARENTS

The seed and pollen parents of 'AUSyacht' are two unnamed seedlings. The new rose may be distinguished from its seed parent, by the following combination of characteristics: the seed parent has a deeper cup and a dark pink color compared with the deep red and flatter bloom of 'AUSyacht'. The new rose may be distinguished from its pollen parent, by the following combination of characteristics: the parent is also red, but is more cupped with fewer petals than 'AUSyacht'.

COMPARISON WITH THE CLOSEST COMMERCIALLY AVAILABLE CULTIVAR

The closest commercially available cultivars to the new variety are the 'AUSchariot' (U.S. Plant Pat. No. 22,206). The new rose may be distinguished from the 'AUSchariot' variety by the following combination of characteristics: the 'AUSchariot' slightly larger blooms which are more domed in shape, whereas the blooms of 'AUSyacht' are a more flat-topped cup shape which flattens with age. In addition, 'AUSchariot' is much more fragrant than 'AUSyacht' having quite a strong musk fragrance compared with a very light tea fragrance of 'AUSyacht'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSyacht' specimens were made at the nursery at David Austin Roses Limited in Albrighton, Wolverhampton, United Kingdom. The following description is of 6 year-old potted rose plants, shown in the illustrations, of the new variety grown indoors in a greenhouse in Albrighton, Britain in the month of June. Phenotypic expression may vary with environmental, cultural and climatic conditions, as well as differences in conditions of light and soil.

Flower characteristics:

*Blooming habit*.—Continuous. The number of blooms per plant during the growing season is profuse, but there are too many to count.

*Bud*.—Size: About 2.2 cm long and 1.8 cm in diameter when the petals start to unfurl. Form: The bud form is pointed ovoid. Color: When sepals first divide, the bud color is RHS 59B (red-purple group). When half blown, the upper sides of the petals are RHS 46A (red group), and the lower sides of the petals are RHS 60A (red-purple group). Calyx: Shape: star-shaped when the bloom is open and folding back against the stem. Length: 7 cm. Diameter: 7 cm. Sepals: Arrangement: Regularly arranged. Color: Upper Surface: green RHS 143C (green group). Lower Surface: green RHS 143B (green group). Length: 3 cm. Width: 1.3 cm. Shape: Lanceolate. Surface texture: Upper Surface: Downy. Lower Surface: Downy. Number: There are 2 heavily appendaged sepals, and 3 unappendaged sepals with hairy edges. Receptacles: Color: RHS 143B (green group). Shape: funnel. Size: broad, about 1 cm high×1.3 cm wide. Surface: Smooth. Peduncle: Length: medium, averaging about 5 cm. Surface: Rough. Color: RHS 143B (green group). Strength: Strong.

*Blooms*.—Size: Medium, average open diameter is about 7 cm. Borne: Mostly singly. (Note: the inflorescence when the shrub is growing naturally may hold between 1 and 4 blooms, and then has a rounded shape. When grown commercially for cut-flower production the stems are disbudded to ensure the blooms are grown singly.) Stems: Strength: Strong, average length is about 90 cm. Diameter: 7 mm. Form: When first open, bloom is cupped. Permanence of bloom: flattens and outer petals curl back.

*Petalage*.—Number of petals under normal conditions: 120. Color: The upper sides of the petals are RHS 60A (red-purple group). The reverse sides of the petals are RHS 60B (red-purple group). The base of the outer petals has RHS 155B (white group). Variegations: None. Discoloration: The general tonality at the end of the first day is RHS 60A (red-purple group), and at the end of the third day is RHS 60A (red-purple group). Fragrance: Very light. Character of fragrance: tea.

*Petals*.—Texture: Velvety. Size: Width: 34 mm. Length: 40 mm. Surface: Smooth. Shape: Obovate. Margin: Mostly entire, but with some frilled and some recurved. Apex Shape: Rounded. Base Shape: Obtuse. Form: Tips slightly recurved. Arrangement: Regular. Petaloids: Number: about 15. Color: RHS 60A (red-purple group). Length: 13 mm. Width: 9 mm. Shape: Ovate, but curled over. Margin: Frilled. Persistence: Petals hang on and dry. Lastingness: On the plant: not tested. As a cut flower: About 10 days.

*Reproductive parts*.—Stamens: Number: 6. Length: 6 mm. Anthers: Length: 4 mm. Color: RHS 16C (yellow-orange group). Arrangement: Mixed with petaloids. Filaments: Color: RHS 16C (yellow-orange group). Length: 4 mm. Pollen: Color: RHS 16A (yellow-orange group). Amount: scarce. Pistils: Number: 60. Length: 13 mm. Styles: Color: RHS 157A (green-white group) tinged with pink (RHS 62A (red-purple group). Length: 11 mm. Stigmas: Color: RHS 155B (white group). Length: 1.5 mm. Hips: None Observed.

Plant characteristics:

*Plant form*.—Shrub.

*Plant growth*.—Medium.

*Age to maturity*.—Two years.

*Mature plant*.—Height: 1 m 30 cm. Width: 60 cm.

*Rootstock*.—*Rosa* 'Inermis' for the observed plants.

*Foliage*.—Number: Leaflets on normal mid-stem leaves is: 3. Size: Large, about 21 cm long×17 cm wide. Quantity: Abundant. Number of leaves per flowering stem is: 12. Color: New foliage: Upper side: RHS 59B (red-purple group) with RHS 144A (yellow-green group). Lower side: RHS 59B (red-purple group). Old foliage: Upper side: RHS 139A (green group). Lower side: RHS 139B (green group).

*Leaflets*.—Size: About 10 cm long×5.5 cm wide. Shape: Ovate. Base Shape: Cordate. Apex Shape: Acuminate. Texture: Leathery. Edge: Serrated. Serrations: Single. Petiole: Color: RHS 137B (green group). Length: 6 cm. Width: 2 mm. Surface Texture: Smooth with small occasional prickles underneath. Strength: medium. Petiole Rachis: Color: RHS 137B (green group). Underside: with prickles. Stipules: Length: 2.5 cm. Color: RHS 137B (green group). Texture: glandular. Auricle: Shape: Lanceolate. Length: 8 mm. Width: 1 mm. Color: RHS 137B (green group). Vein Color: Same as leaf color. Venation Pattern: Reticulate.

*Wood*.—New Wood: Color: RHS 59B (red-purple group). Bark: Smooth. Old Wood: Color: RHS 143C (green group). Bark: Rough.

*Branching habit*.—Number: None.

*Stems*.—Mature Stem: Length: 90 cm. Diameter: 7 mm. Internode Distance: 6 cm. The above measurements are all variable, depending on growing conditions in a season. Stem Pubescence Present: No.

*Prickles*.—Quantity: On main canes from base: Ordinary. Number per stem length: 13 per 10 cm. Form: Deep concave. Length: 6 mm. Color when young: RHS 181A (greyed-red group). Color when mature: RHS 195B (greyed-green group).

*Small prickles*.—Quantity: Main stalk: None. Laterals: None.

*Disease resistance*.—Mildew: Resistant (*Podosphaera pannosa*). Blackspot: Not tested (*Diplocarpon rosae*). Rust: Not tested (*Phragmidium tuberculatum*).

*Pest resistance*.—Not tested.

*Winter hardiness*.—Not tested.

*Growing conditions*.—Normal greenhouse conditions.

What is claimed is:

1. A new and distinct variety of rose plant of the shrub class suitable for cut flower production, substantially as herein shown and described.

* * * * *

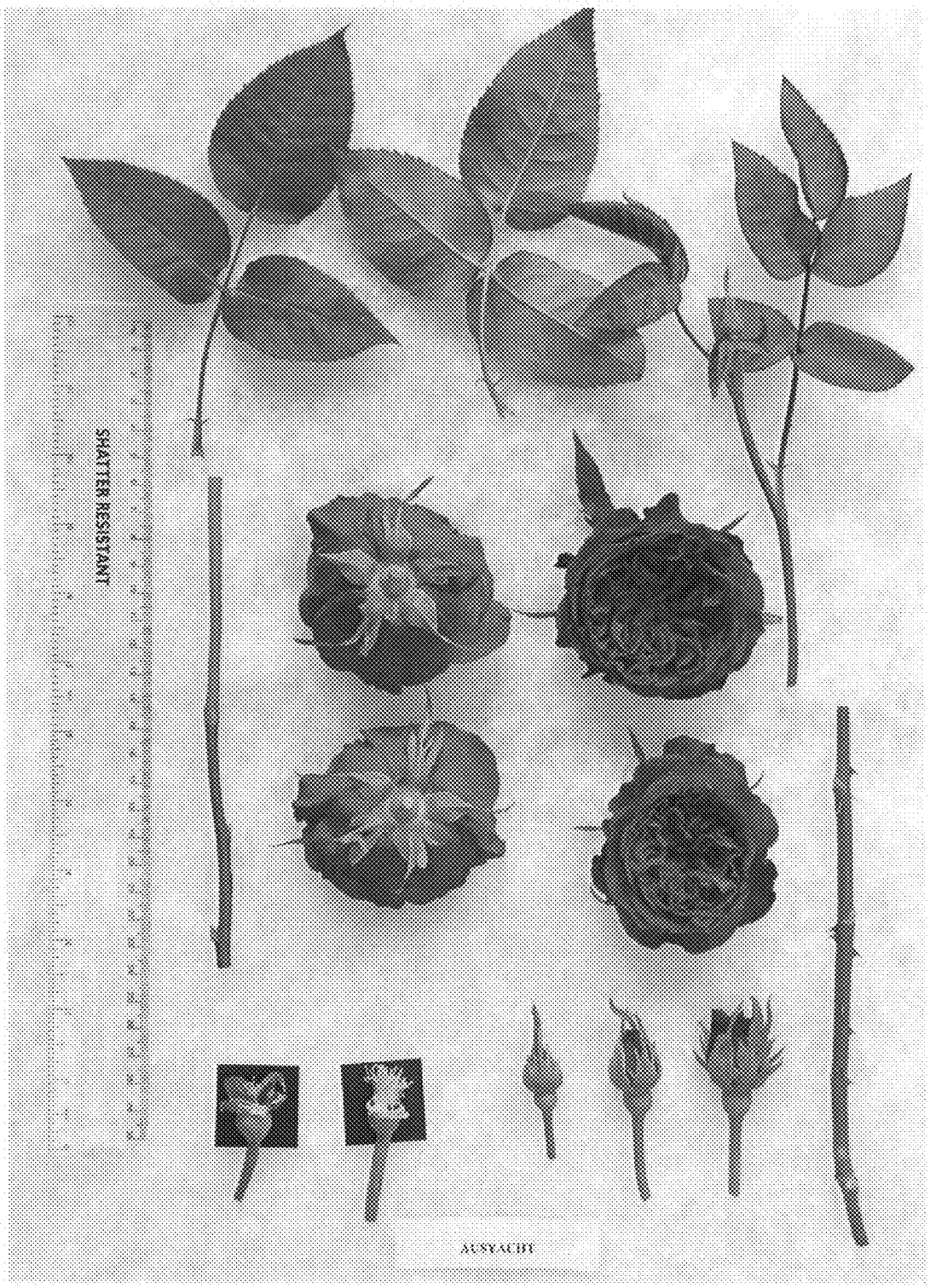
SHATTER RESISTANT
AUSYAUBE